(12) United States Patent
Ono

(10) Patent No.: US 7,828,718 B2
(45) Date of Patent: Nov. 9, 2010

(54) PENIS EXERCISE MACHINE

(75) Inventor: Hiroyuki Ono, Urayasu (JP)

(73) Assignee: Main Ltd., Chiba-ken (JP)

( * ) Notice: Subject to any disclaimer, the term of this patent is extended or adjusted under 35 U.S.C. 154(b) by 2 days.

(21) Appl. No.: 12/220,127

(22) Filed: Jul. 22, 2008

(65) Prior Publication Data

US 2009/0247377 A1    Oct. 1, 2009

(30) Foreign Application Priority Data

Mar. 31, 2008    (JP) .............................. 2008-089228

(51) Int. Cl.
*A61F 5/00*    (2006.01)
(52) U.S. Cl. ....................................................... 600/38
(58) Field of Classification Search ............. 600/38–41; 128/897, 898
See application file for complete search history.

(56) References Cited

U.S. PATENT DOCUMENTS

2004/0215055 A1* 10/2004 Gomez-de-Diego .......... 600/38

FOREIGN PATENT DOCUMENTS

| JP | 2001-519206 | | 10/2001 | | |
| WO | WO 96/26691 | * | 9/1996 | .................. | 600/38 |
| WO | WO 97/28764 | * | 8/1997 | .................. | 600/38 |

* cited by examiner

*Primary Examiner*—Samuel G Gilbert
(74) *Attorney, Agent, or Firm*—Jordan and Hamburg LLP

(57) ABSTRACT

A penis exercise machine includes an attaching portion main body which is abutted against and mounted on a body surface side of a periphery of a man's penis, a pair of support rods whose one ends are turnably mounted on a surface of the attaching portion main body such that the support rods are located on both sides sandwiching the penis, a support portion which is mounted such that it can be attached to both end sides of the support rods and which is abutted such that a glans on the side of a tip end of the penis is supported, and a holding belt of the glans mounted on the support portion.

5 Claims, 5 Drawing Sheets

PENIS EXERCISE MACHINE

BACKGROUND OF THE INVENTION

1. Field of the Invention

The present invention relates to a penis exercise machine which is attached to a man's penis portion so as to expand a penis body without pain while holding a glans side of the penis.

2. Description of the Related Art

A conventional penis exercise machine used for expanding a penis has such a structure that an expanding force generated by a belt for holding a glans is concentrated on the glans. Therefore, an initial action is hard and a user is prone to feel pain, and if the penis exercise machine is used for a long time, the user may feel pain, and it is necessary to reattach the penis exercise machine at abut one hour intervals. Therefore, the number of attaching and detaching times of the penis exercise machine is increased, and it is inconvenient to use the machine at a workplace during the daytime.

In relation to a conventional penis expansion device, there is disclosed a penis expansion device having a drawing element extending between a fixing device for fixing a penis glans and a receiver of a penis root functioning as a stretching support (see, for example, Patent Document 1).

[Patent Document 1] Japanese Patent Application Laid-Open No. 2001-519206

SUMMARY OF THE INVENTION

The present invention has been accomplished in view of the above circumstances, and it is an object of the invention to provide a penis exercise machine which does not generate strong pull-in action that may cause pain when a penis is expanded at an initial stage, which can be used even by a beginner for a long time with small pain, and which is not detached easily.

To achieve the above object, an invention according to a first aspect provides a penis exercise machine including: an attaching portion main body which is abutted against and mounted on a body surface side of a periphery of a man's penis; a pair of support rods whose one ends are turnably mounted on a surface of the attaching portion main body such that the support rods are located on both sides sandwiching the penis; a support portion which is mounted such that it can be attached to both end sides of the support rods and which is abutted such that a glans on the side of a tip end of the penis is supported; and a holding belt of the glans mounted on the support portion. Since the support portion abuts such that the glans on the side of the tip end of the penis is supported. Therefore, strong pull-in action which may cause pain when a penis is expanded at an initial stage is not generated, even a beginner can use the machine for a long time with small pain, and the machine is not detached easily.

In an invention according to a second aspect, the pair of support rods is formed such that lengths thereof can be adjusted in accordance with a length of the penis, and the support rods are formed such that they can be pushed toward the attaching portion main body against a biasing force of a spring. Since the length can be adjusted in accordance with a length of a penis, anyone can use the machine.

In an invention according to a third aspect, the pair of support rods is formed into such a mechanism that shortened states of the support rods can be maintained by locking a state when the support rods are pushed toward the attaching portion main body against a biasing force of the spring. Since the shortened state is maintained by locking, expansion of a penis can temporarily be stopped.

In an invention according to a fourth aspect, the support portion is formed into a recessed holder against which a back surface side of the glans abuts. Since the support portion is formed into the recessed holder, a back surface of the glans can reliably be held without pain.

In an invention according to a fifth aspect, the holding belt of the glans mounted on the support portion is mounted such that the holding belt can be adjusted so as to hold the penis depending on a size of the glans. Since the holding belt can be adjusted in accordance with the size of the glans, the machine can be used appropriately.

The penis exercise machine includes an attaching portion main body which is abutted against and mounted on a body surface side of a periphery of a man's penis, a pair of support rods whose one ends are turnably mounted on a surface of the attaching portion main body such that the support rods are located on both sides sandwiching the penis, a support portion which is mounted such that it can be attached to both end sides of the support rods and which is abutted such that a glans on the side of a tip end of the penis is supported, and a holding belt of the glans mounted on the support portion. With this configuration, strong pull-in action which may cause pain when a penis is expanded at an initial stage is not generated, even a beginner can use the machine for a long time with small pain, and the machine is not detached easily.

DETAILED DESCRIPTION OF THE INVENTION

Figure 1:
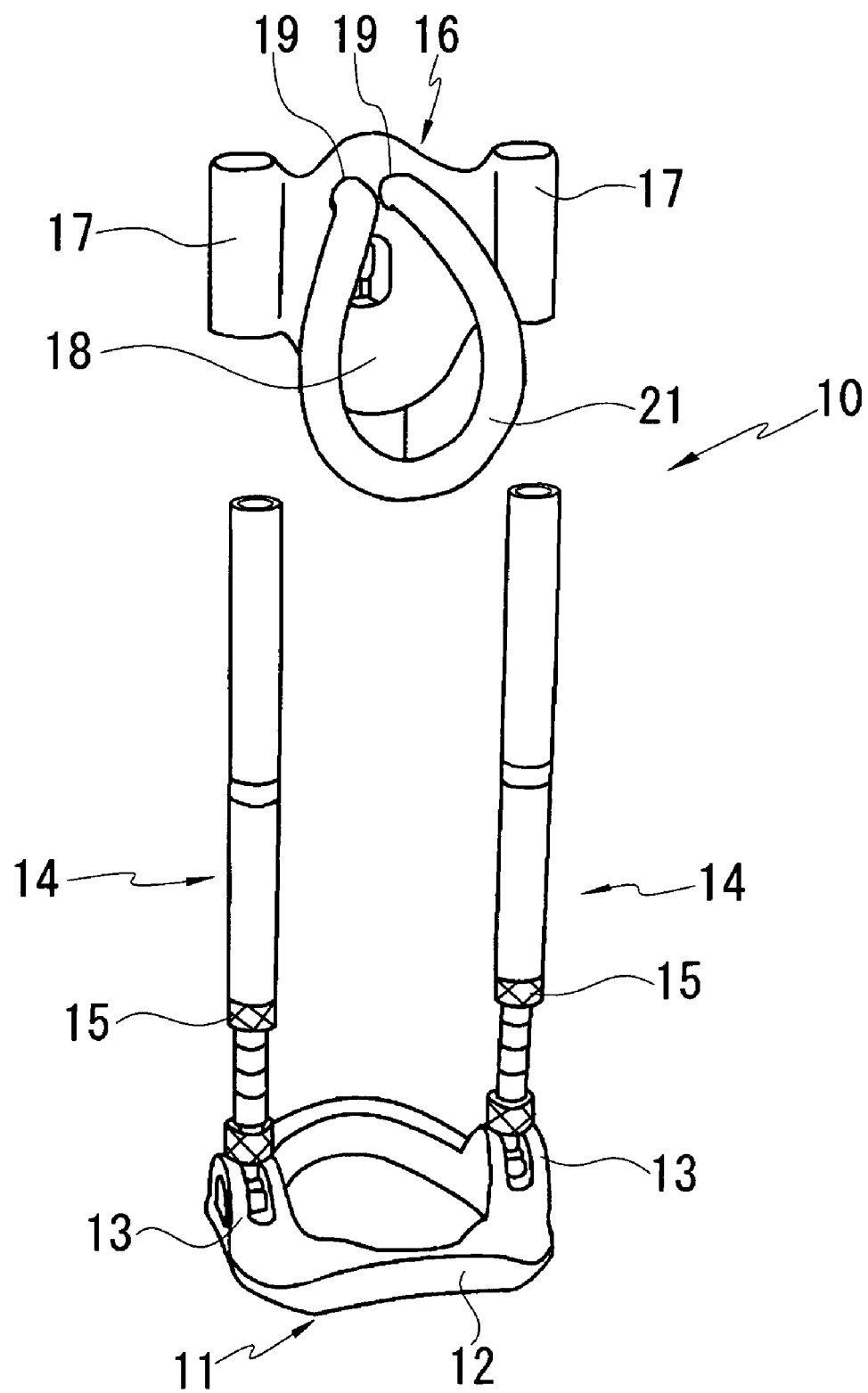
FIG. 1 is a perspective view of an upper face of a penis exercise machine according to an embodiment of the present invention from which a holder is detached.
Figure 2:
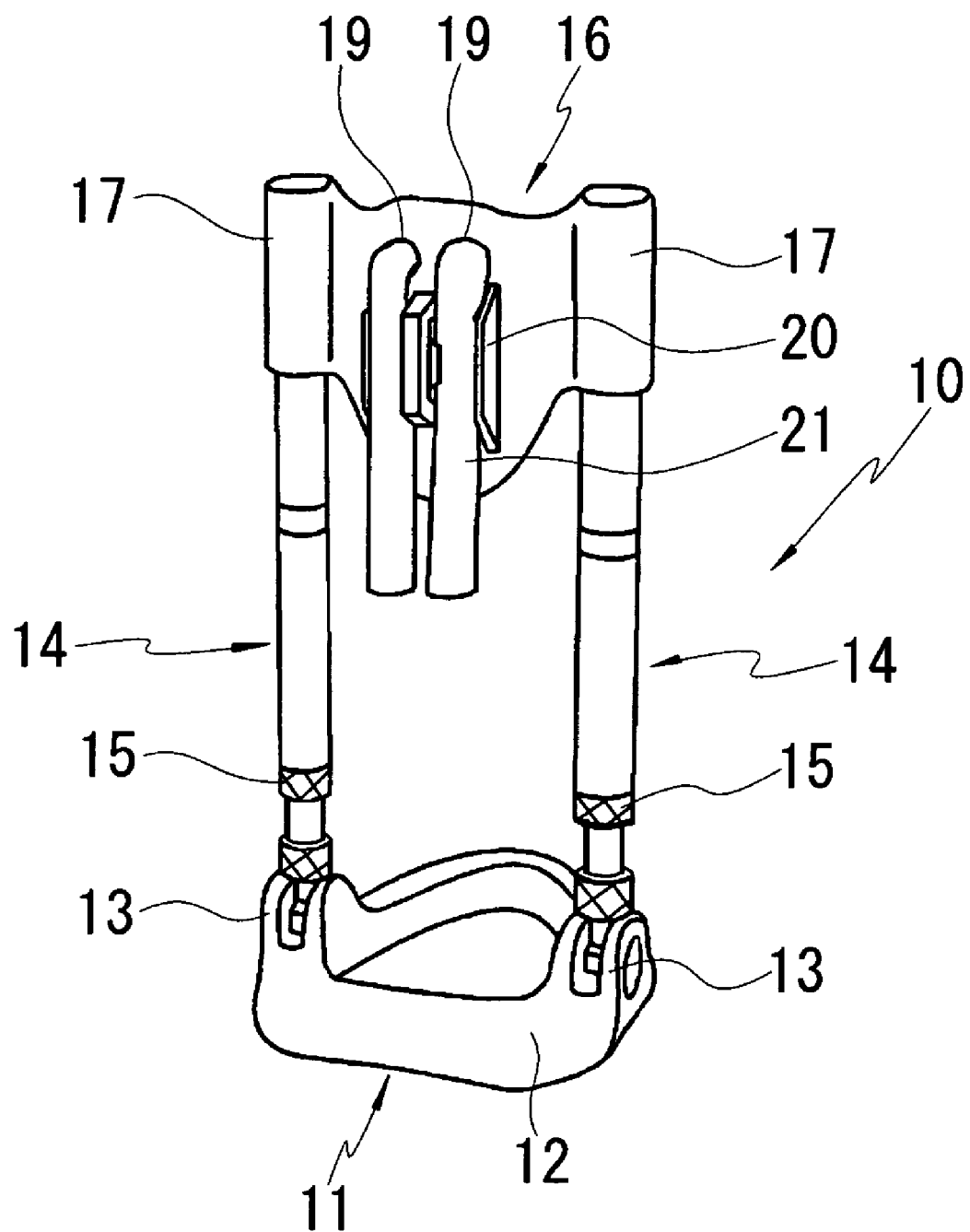
FIG. 2 is a perspective view of a lower face of the penis exercise machine according to the embodiment of the invention to which the holder is attached.

An illustrated embodiment of the present invention will be explained below more concretely. FIGS. 1 and 2 are diagrams for explaining a penis exercise machine according to the embodiment of the invention, wherein FIG. 1 is a perspective view of an upper face of the penis exercise machine from which a holder is detached, and FIG. 2 is a perspective view of a lower face of the penis exercise machine to which the holder is attached. The operation in the attaching state will be explained with reference to subsequent drawings.

A penis exercise machine 10 according to the embodiment of the invention is a machine which is attached to a portion of a man's penis 1 so as to expand the penis. Here, a portion of the penis 1 on the side of a human body is called penis root 2, a portion of the penis 1 on the side of its tip end is called glans 4, and a portion of the penis 1 between the penis root 2 and the glans 4 is called penis body 3. The penis exercise machine 10 includes an attaching portion main body 11 which is abutted against a body surface around the penis root 2 and attached thereto, a pair of support rods 14 and 14 mounted on a surface of the attaching portion main body 11 such that one ends of the support rods 14 and 14 can turn so as to be located on both sides to sandwich the penis 1, a support portion 16 which can be attached to both ends of the support rods 14 and 14, and a holding belt 21 of the glans 4 which can be attached to the support portion 16. In FIG. 1, the support rods 14 and 14 are expanded or contracted by springs, and the support portion 16 is detached from both ends of the support rods 14 and 14. In FIG. 2, the support rods 14 and 14 are brought into a pull-down locked state against expansion of the springs, and the support portion 16 is attached to the both ends of the support rods 14 and 14.

The attaching portion main body 11 is made of resin material such as plastic, covers a periphery on the side of the penis root 2 with a sufficient area, and has a substantially circular ring-like shaped attaching ring 12 which is abutted against a surface on the side of a body. An inner diameter of the attaching portion main body 11 is in the range of 4 to 5 cm, and an outer diameter thereof is in the range of about 6 to 7 cm. Mounting portions 13 and 13 for turnably attaching the pair of later-described support rods 14 and 14 are formed on the side of a surface of the attaching ring 12 of the attaching portion main body 11. The mounting portions 13 and 13 are formed to be on left and right sides sandwiching the penis root 2 when the attaching portion main body 11 is attached.

The support rods 14 and 14 are made of shaft-like material having the same length such as metal material. One ends of the support rods 14 and 14 are turnably mounted on the mounting portions 13 and 13. The support rod 14 is a shaft-like body having an outer diameter of about 8 to 10 mm, and a length thereof can be adjusted by threadedly mounting an additional support rod into the other end in accordance with a length of the penis 1. Materials such as springs (not shown) are inserted into the mounting portions 13 and 13 of the support rods 14 and 14 to form expandable towing portions 15 and 15. The support rods 14 and 14 can be pushed into the attaching portion main body 11 against the biasing forces of springs by about 1.5 to 2 cm, and if the pushed state can be locked, the shortened state can be held, and if this locked state is unlocked, it can be expanded by the spring from the held state.

The support portion 16 is mounted on the ends of the support rods 14 and 14, and the glans 4 abuts against the support portion 16 to hold the glans 4. The support portion 16 is made of resin material such as plastic like the attaching portion main body 11, mounting portions 17 and 17 into which ends of the support rods 14 and 14 are inserted are formed, a recessed holder 18 against which a back surface of the glans 4 abuts is formed between these mounting portions 17 and 17, a pair of mounting holes 19 and 19 is formed for mounting a holding belt 21 of the glans 4 on an end of the holder 18 opposite from the attaching portion main body 11, and a back surface of the support portion 16 is formed with holding belt fixing portions 20 and 20 for attaching both ends of the holding belt 21 attached to the mounting holes 19 and 19 so that the ends are not pulled out.

The holding belt 21 is inserted into the mounting holes 19 and 19 of the support portion 16 to be mounted in a form of a ring and used in this form. The holding belt 21 is a soft and circular thick tube having an outer diameter of 6 to 7 mm, an inner diameter of about 1 to 2 mm, and length of about 20 to 30 cm made of silicon rubber.

Figure 3:
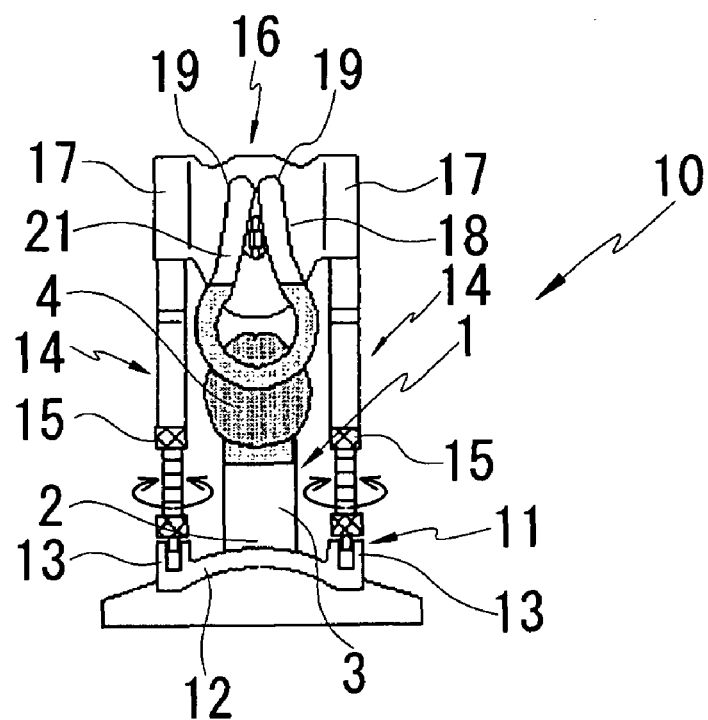
FIG. 3 is a diagram for explaining a state before the machine of the embodiment of the invention is attached.
Figure 4:
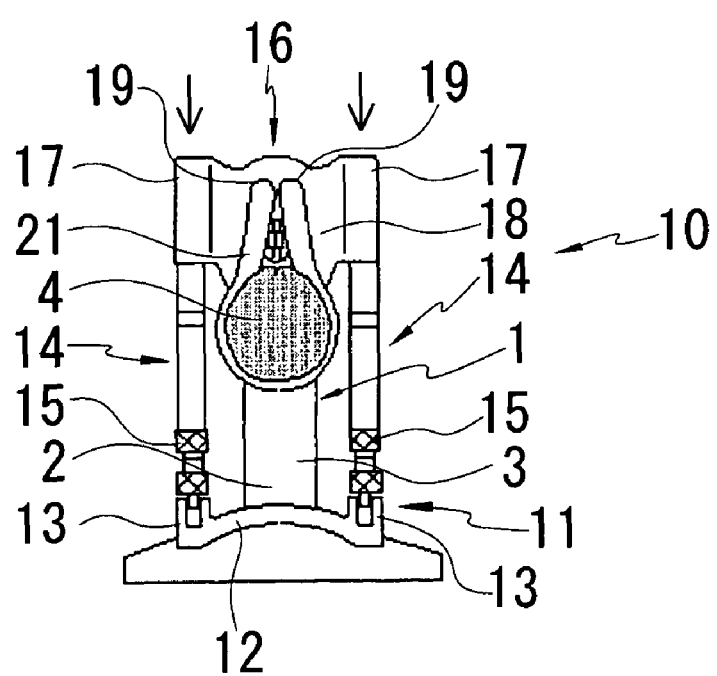
FIG. 4 is a diagram for explaining a holding state of a glans when the machine according to the embodiment of the invention is attached.
Figure 5:
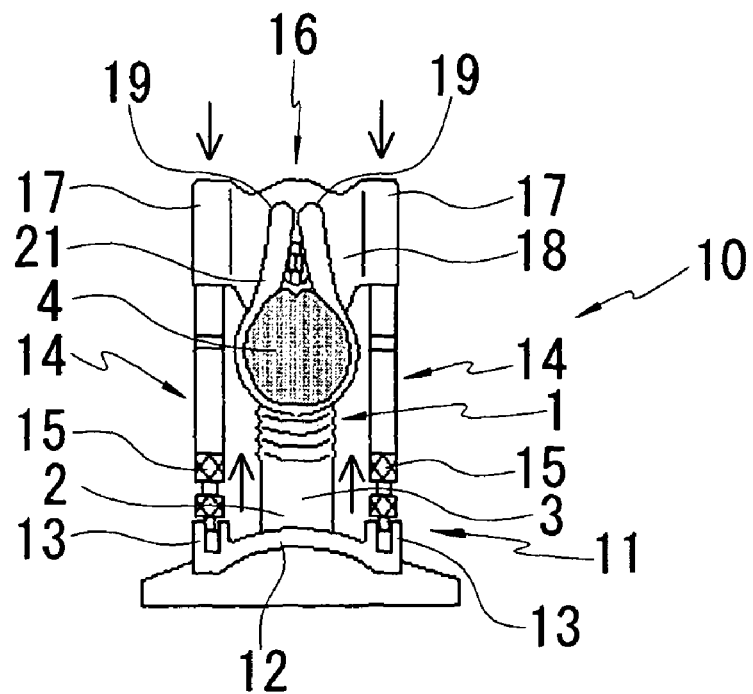
FIG. 5 is a diagram for explaining a processing state of a penis after the machine according to the embodiment of the invention is attached.
Figure 6:
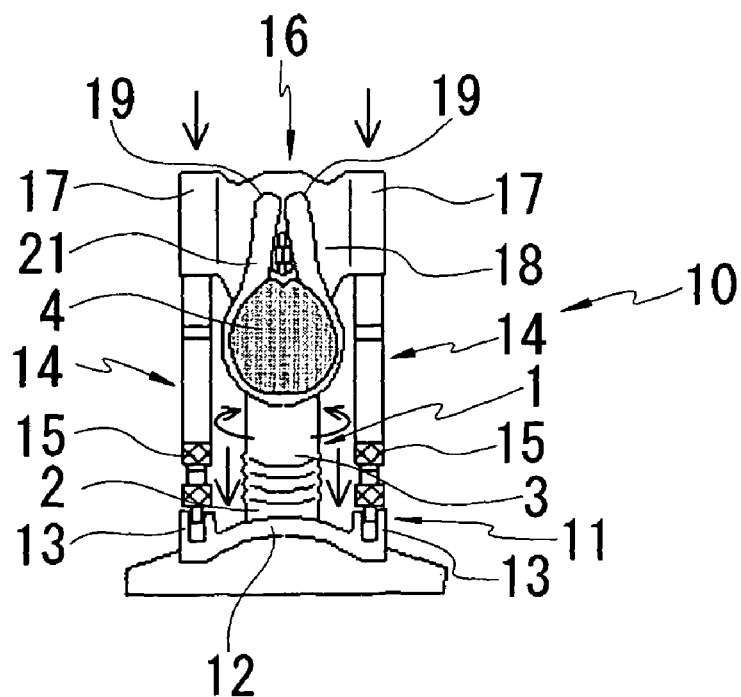
FIG. 6 is a diagram for explaining a processing state subsequent to the penis processing after the machine according to the embodiment of the invention is attached.
Figure 7:
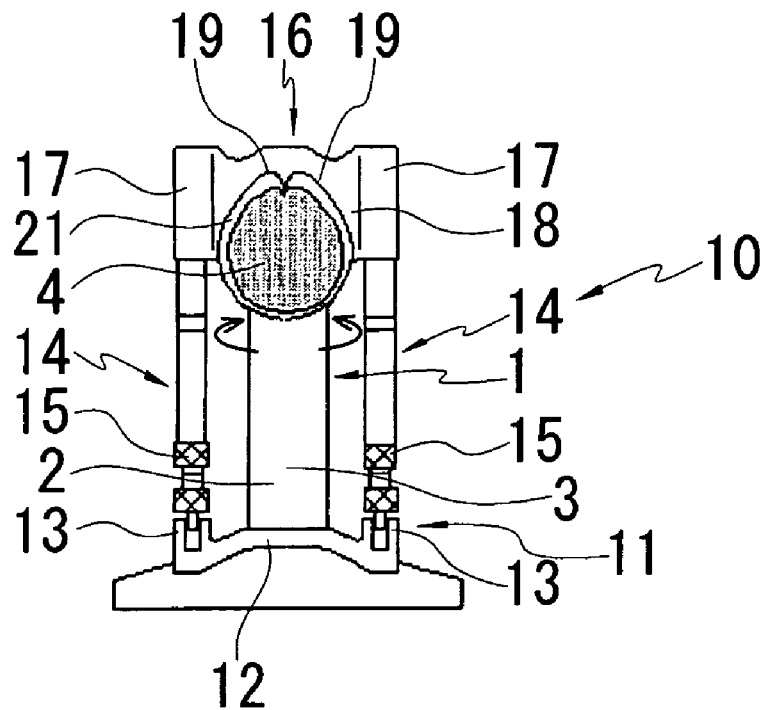
FIG. 7 is a diagram for explaining an attaching state of the machine according to the embodiment of the invention.
Figure 8:
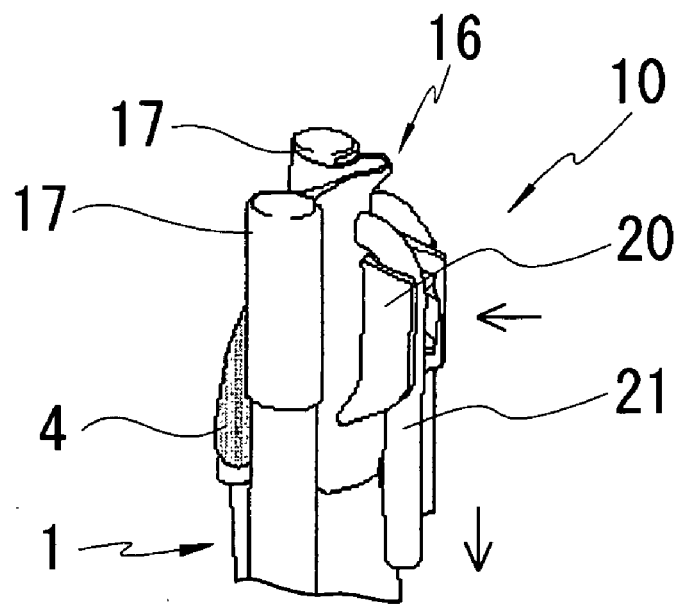
FIG. 8 is a diagram for explaining a fixing state of a belt in the attaching state of the machine according to the embodiment of the invention.

Next, a method of using the penis exercise machine 10 including attaching procedure will be explained. FIG. 3 is a diagram for explaining a state before the machine is attached. FIG. 4 is a diagram for explaining a holding state of a glans when the machine is attached. FIG. 5 is a diagram for explaining a processing state of a penis after the machine is attached. FIG. 6 is a diagram for explaining a processing state subsequent to the penis processing after the machine is attached. FIG. 7 is a diagram for explaining an attaching state. FIG. 8 is a diagram for explaining a fixing state of a holding belt in the attaching state.

First, to start using the penis exercise machine 10 of the present invention, the towing portions 15 and 15 are brought into an expandable state by the springs, and the support rods 14 and 14 having such lengths that a position of the penis 1 approaches the holder 18 are used. Next, baby powder or the like is previously applied to a ring-like portion to which the holding belt 21 is attached and a surface of the glans 4 before the machine is attached. The baby powder is applied in a dry state instead of wet state so that the machine is not easily detached. Next, as shown in FIG. 3, the penis 1 is inserted into the attaching ring 12 of the attaching portion main body 11 from the glans 4, and the penis 1 abuts against a surface of a body side and attached.

Next, as shown in FIG. 4, the side of the support portion 16 is pushed into the side of the attaching portion main body 11 against biasing forces of the springs of the support rods 14 and 14 on the side of the towing portions 15 and 15, the glans 4 is inserted into the ring portion of the holding belt 21, and the machine is attached such that a back surface of the glans 4 is abutted against the recessed holder 18.

Next, as shown in FIG. 5, the pushing action of the springs is held and in this state, a skin of the penis body 3 is pulled up toward the glans 4. This is because, if the holding belt 21 is fastened, the spring force is strong, and thus the skin of the penis body 3 on the side of the penis root 2 cannot be pulled out or the pulled out glans 4 is detached.

Next, as shown in FIG. 6, while the pushing action of the springs is held, the skin pulled up from the penis root 2 side toward the penis body 3 and the skin of a lower portion of the glans 4 are pulled and a wrinkle is stretched. Here, if the pushing state of the spring is reliably maintained, it does not return toward a body. If the holding belt 21 is fastened with the wrinkle, a thin skin is folded back and a user feels pain, and further an abrasion may be produced.

Next, as shown in FIG. 7, the holding belt 21 is pulled and fastened from the back surface of the holder 18 while maintaining the push-in action of the spring. At this time, it is important to pull the holding belt 21 such that a wrinkle is not generated in a lower contact portion of the glans 4 with respect to the holding belt 21. If the glans 4 is pinched immediately before the holding belt 21 is fastened to pull the glans 4 toward the body side, the penis is less prone to be pulled out.

Next, as shown in FIG. 8, while the holding belt 21 which is pulled out toward the back surface of the holder 18 is pressed, the holding belt 21 is pushed against the holding belt fixing portions 20 and 20 and fixed. In this state, only the penis 1 is pulled, and an outer skin should have a margin. If the outer skin is stretched, it is difficult to pull out a skin on the side of the penis root 2 after the attaching ring 12 is pressed against the pulled penis root 2 and thus, the operation must be done from the beginning.

As explained above, the penis exercise machine 10 according to the embodiment of the present invention includes the attaching portion main body 11 which is abutted against and mounted on a body surface side of a periphery of the man's penis 1, the pair of support rods 14 and 14 whose one ends are turnably mounted on a surface of the attaching portion main body 11 such that the support rods 14 and 14 are located on both sides sandwiching the penis 1, the support portion 16 which is mounted such that it can be attached to both end sides of the support rods 14 and 14 and which is abutted such that the glans 4 on the side of a tip end of the penis 1 is supported, and the holding belt 21 of the glans 4 mounted on the support portion 16. With this configuration, strong pull-in action which may cause pain when a penis is expanded at an initial stage is not generated, even a beginner can use the machine for a long time with small pain, and the machine is not detached easily.

The invention provides a penis exercise machine which does not generate strong pull-in action that may cause pain when a penis is expanded at an initial stage, which can be used even by a beginner for a long time with small pain, and which is not detached easily.

What is claimed is:

1. A penis exercise machine comprising:
    an attaching portion main body configured to be abutted against and mounted on a body surface side of a periphery of a man's penis;
    a pair of support rods comprising ends thereof which are turnably mounted on a surface of the attaching portion main body such that the support rods are located across from one another so as to be configured for placement of the penis therebetween, each of the rods biased in a direction toward or away from the attaching portion main body so that the rods are adjustable in a lengthwise direction without rotation of the rods;
    a support portion which is removably mounted to ends of the support rods which are opposite the ends thereof which are mounted on the attaching portion main body, and which is configured to be abutted such that a glans on the side of a tip end of the penis is supported; and
    a holding belt of the glans mounted on the support portion, positioning of the support portion relative to the attaching portion main body being provided only by the biased adjustment of the rods.

2. The penis exercise machine according to claim 1, wherein the pair of support rods is formed such that lengths thereof can be adjusted in accordance with a length of the penis, and the support rods are formed such that they can be pushed toward the attaching portion main body against a biasing force of a spring.

3. The penis exercise machine according to claim 2, wherein the pair of support rods is formed into such a mechanism that shortened states of the support rods can be maintained by locking a state when the support rods are pushed toward the attaching portion main body against a biasing force of the spring.

4. The penis exercise machine according to claim 1, wherein the support portion is formed into a recessed holder configured to receive and support a back surface side of the glans.

5. The penis exercise machine according to claim 1, wherein the holding belt of the glans mounted on the support portion is mounted such that the holding belt can be adjusted so as to hold the penis depending on a size of the glans.

\* \* \* \* \*